(12) United States Patent
Maas

(10) Patent No.: US 9,085,397 B2
(45) Date of Patent: Jul. 21, 2015

(54) ASSEMBLY AND METHOD FOR INTRODUCING A DOSE OF A MIXING SUBSTANCE INTO A CONTAINER

(75) Inventor: Bartholomeus Henricus Antonius Maas, Elst (NL)

(73) Assignee: EUROTROL B.V., Ede (NL)

( * ) Notice: Subject to any disclaimer, the term of this patent is extended or adjusted under 35 U.S.C. 154(b) by 1447 days.

(21) Appl. No.: 12/083,199

(22) PCT Filed: Oct. 6, 2006

(86) PCT No.: PCT/NL2006/000506

§ 371 (c)(1),
(2), (4) Date: Apr. 7, 2008

(87) PCT Pub. No.: WO2007/040396

PCT Pub. Date: Apr. 12, 2007

(65) Prior Publication Data

US 2009/0065378 A1    Mar. 12, 2009

(30) Foreign Application Priority Data

Oct. 6, 2005  (NL) .................................... 1030129

(51) Int. Cl.
*G01F 11/00* (2006.01)
*B65D 51/22* (2006.01)
(Continued)

(52) U.S. Cl.
CPC ............. *B65D 51/222* (2013.01); *A61J 1/2089* (2013.01); *B01L 3/502* (2013.01); *B65D 50/06* (2013.01); *B65D 51/2864* (2013.01); *G01F 11/10* (2013.01); *G01F 19/00* (2013.01); *A61J 2001/201* (2013.01); *A61J 2001/2051* (2013.01);

(Continued)

(58) Field of Classification Search
CPC ....... G01F 11/02; G01F 11/10; G01F 11/027; G01F 11/028; G01F 11/82; B01L 2300/049; B01L 2400/0478; B01L 2400/0481
USPC .......... 206/219, 222, 145, 568; 222/417, 448, 222/454; 141/22, 320, 321, 322; 426/115, 426/120
See application file for complete search history.

(56) References Cited

U.S. PATENT DOCUMENTS 3,894,661 A * 7/1975 Guala ........................... 222/188
4,151,934 A * 5/1979 Saeki ........................... 222/437

(Continued)

FOREIGN PATENT DOCUMENTS

DE        197 11 954 A1    10/1997
GB        1 479 370 A       7/1977

(Continued)

*Primary Examiner* — Anthony Stashick
*Assistant Examiner* — Ernesto Grano
(74) *Attorney, Agent, or Firm* — Birch, Stewart, Kolasch & Birch, LLP

(57) ABSTRACT

The present invention provides an assembly for introducing a dose of a mixing substance into a container, said assembly comprising a dosing part (3) and a supply part (2), which dosing part is arranged for receiving the dose and which supply part comprises an outlet (14) for introducing the dose into the container. The dosing part and the supply part are configured to cooperate with one another, such that a pressure chamber having a changeable volume is formed adjacent to the outlet when the supply part and the dosing part are joined together, which pressure chamber functions to enable a pumping action for pumping the dose into and out of the container. The invention further provides a method for inserting such a dose into a container.

23 Claims, 6 Drawing Sheets

(51) Int. Cl.
*A61J 1/20* (2006.01)
*B65D 50/06* (2006.01)
*B65D 51/28* (2006.01)
*G01F 11/10* (2006.01)
*G01F 19/00* (2006.01)
*B01L 3/00* (2006.01)

(52) U.S. Cl.
CPC ......... *A61M 2207/00* (2013.01); *B01L 3/50825* (2013.01); *B01L 2300/047* (2013.01); *B01L 2300/049* (2013.01); *B01L 2400/0478* (2013.01); *B01L 2400/0481* (2013.01)

(56) References Cited

U.S. PATENT DOCUMENTS

| | | | | | |
|---|---|---|---|---|---|
| 4,201,316 | A | * | 5/1980 | Klingaman | 222/80 |
| 4,315,570 | A | * | 2/1982 | Silver et al. | 206/221 |
| 4,526,294 | A | * | 7/1985 | Hirschmann et al. | 222/47 |
| 4,821,930 | A | * | 4/1989 | Luine et al. | 222/454 |
| 4,886,193 | A | * | 12/1989 | Wassilieff | 222/446 |
| 5,114,411 | A | * | 5/1992 | Haber et al. | 604/203 |
| 5,335,773 | A | * | 8/1994 | Haber et al. | 206/221 |
| 5,407,104 | A | * | 4/1995 | Santagiuliana | 222/425 |
| 5,564,600 | A | * | 10/1996 | Renault | 222/129 |
| 5,927,354 | A | * | 7/1999 | Flewitt | 141/381 |
| 6,068,165 | A | * | 5/2000 | Minihane et al. | 222/454 |
| 6,321,908 | B1 | * | 11/2001 | Lorscheidt | 206/221 |
| 6,375,460 | B1 | * | 4/2002 | Plaumann | 433/80 |
| 6,702,161 | B2 | * | 3/2004 | Adams et al. | 222/521 |
| 2002/0185125 | A1 | * | 12/2002 | Klimowicz et al. | 128/200.16 |

FOREIGN PATENT DOCUMENTS

| | | |
|---|---|---|
| GB | 1 522 890 A | 8/1978 |
| JP | 7-223681 A | 8/1995 |
| WO | WO-93/25446 A1 | 12/1993 |

\* cited by examiner

Connecting part with inlet to receive 15 and connect to a container

ASSEMBLY AND METHOD FOR INTRODUCING A DOSE OF A MIXING SUBSTANCE INTO A CONTAINER

TECHNICAL FIELD OF THE INVENTION

The present invention relates to an assembly for introducing a dose of a mixing substance into a container, said assembly comprising a dosing part and a supply part, which dosing part is arranged for receiving the dose and which supply part comprises an outlet for introducing the dose into the container.

The invention further relates to a method for introducing a dose of a mixing substance into a container by means of an assembly as described above, which assembly comprises a dosing part and a supply part, which supply part comprises an outlet for introducing the dose into the container.

BACKGROUND OF THE INVENTION

Such an assembly is known in the art and is shown by way of example in FIG. 4. The assembly consists of a dosing part 38 and a supply part 39. The supply part 39 comprises an outlet 40, which is sealed by means of a sealing element 41, which is circumferentially connected to the end of the outlet 40 by means of a weld 42. Note that the parts shown in FIG. 4 are circularly symmetrical in relation to a longitudinal axis through the centre of the illustrated section. The dosing part comprises a dose container 45, in which a dose can be received. The dose container 45 has a wall 46, which is so configured that it can be received in a corresponding wall 47 of the supply part 39.

An outer wall of the dosing part consists of a first wall part 48 and a second wall part 49, which annularly surround the wall 46 of the dose container 45. The first part 48 of the outer wall of the dose container is connected to the second part 49 of the outer wall by means of a multitude of concentrically arranged welds 50. The welds 50 are so dimensioned that the welds can be easily broken by exerting a force on the wall parts 48 and 49.

The assembly is sealed by filling the dose container 45 of the dosing part and sliding the wall 47 of the supply part over the wall 46 of the dosing part 38. The supply part is moved into the dosing part until the receiving part 48 that concentrically surrounds the wall 47 of the supply part abuts against the welds 50 of the dosing part. The end 51 of the wall 47 will slide into the space 53 between the wall 46 of the dose container and the second wall part 49 thereof. The end of the supply part 39, consisting of the outlet 40, is now moved into the filling opening of a correspondingly shaped container (not shown). The supply part 39 is moved into said opening until the edges of the filling opening of the container (not shown) abut against the side 56 of the receiving part 58 of the supply part 39.

The dose that is present in the dose container 45 is transferred in the following manner. When a force is exerted on the assembly via the rear side 52 of the dosing part 38, the welds 50 will be broken by the receiving part 58, as a result of which the second wall part 49 of the dosing part will become detached from the first wall part 48. The force being exerted causes the detached part of the dosing part 38, consisting of the second wall part 49, the rear side 52 and the dose container 46, to move further into the receiving part 58, and the end 55 of the wall 46 of the dose container will perforate the concentric weld 42 of the sealing element 41 of the outlet 40, as a result of which the outlet 40 is opened, so that the dose will flow into the container. In the container, the dose will mix with the container substance that is already present in the container.

A drawback of the prior art assembly as described above is that fluid may remain behind in the dose container 45, for example on the walls and in the corners thereof. In addition, it is not possible to mix the residue of the dose that has remained behind in the dose conveyor 45 with a container substance that is present in the container yet, in particular if the weld 42 has not been completely broken by the end 55 of the wall 46 of the dose container 45. In practice it has become apparent that usually the amount of air that is present in the dose container cannot move out of the dose container 45 if the weld 42 has not been completely broken, so that a barrier is formed, which prevents the dose from flowing back into the dose container. Another problem is that the wall of the dose container shoots through into the container as a result of the weld 42 being broken, forming a physical barrier at that location, which prevents the dose from flowing back.

Another drawback of the prior art assembly is that a relatively large force is required for perforating the weld 42. This has a negative effect on the functionality of the assembly and, in addition, increases the risk of accidents.

Another possibility of mixing a dose with a container substance is to use a pipette. A drawback of such a method is that is not easy, especially for untrained or poorly trained personnel, to introduce a precisely metered dose into the pipette. The job requires experience and skill, and the risk of inaccuracies is great. For example, air bubbles may be drawn along when sucking up a dose, which air bubbles may lead to the volume of the mixing substance being sucked up deviating from the desired volume.

Another drawback is the fact that a precise transfer of the dose from the pipette to the container requires skill as well, and that moreover the viscosity of the fluid plays an important role. If a highly viscous fluid is to be introduced into a container by means of a pipette, there is a great risk of residual fluid remaining behind in the pipette. Residue may remain behind in particular in the conical outlet of a pipette via which the fluid is to be transferred to a container. It is not easy to mix this residue yet with the substance that is present in a container at a later stage.

Yet another drawback of the use of a pipette is the fact that a pipette is not suitable for storing or transporting a dose present therein of a substance that is to be transferred to a container. Consequently, the pipette cannot be used, for example, for supplying a dose of a specific substance that is not available as standard in a laboratory, for example.

The prior art therefore does not provide satisfactory methods and means for transferring a very precisely metered dose to a container without losing part of the dose (for example in the form of residue that remains behind in a pipette or assembly as described above).

SUMMARY OF THE INVENTION

In the light of the foregoing it is the object of the present invention to provide an assembly and a method by means of which a precisely metered dose of a mixing substance can be introduced into a container in its entirety.

According to a first aspect of the invention, this object is accomplished in that the invention provides an assembly for introducing a dose of a mixing substance into a container, said assembly comprising a dosing part and the supply part, which dosing part is arranged for receiving the dose and which supply part comprises an outlet for introducing the dose into the container, characterised in that the dosing part and the supply part are configured to cooperate with one another, such that a pressure chamber having a changeable volume is formed adjacent to the outlet when the supply part and the dosing part are joined together, which pressure chamber functions to enable a pumping action for pumping the dose into and out of the container.

Since a pressure chamber whose volume can be changed is formed adjacent to the outlet by joining the supply part and the dosing part, a pumping action can be obtained between the container and the assembly (in particular the pressure chamber), so that the dose that is present in the assembly can be pumped into the container in its entirety. In addition to that, after the dose has been transferred to the container the mixture of the dose and the container substance that is present in the container can be pumped back into the pressure chamber in a similar manner for the purpose of rinsing out the outlet and the pressure chamber of the assembly. This can be repeated a number of times so as to ensure that the entire dose is mixed with the container substance in the container. Thus it is possible to realise the desired concentration ratio between container substance and mixing substance in a simple and accurate manner, without any risk of leakage of the mixture from the assembly or residue of the dose remaining behind in the assembly.

Moreover, since a separate dosing part and a separate supply part are used, the dose can be easily introduced into the dosing part upon filling the assembly. This makes it possible to verify and possibly adapt the dose after filling of the dosing part, if desired.

According to one embodiment of the invention, the dosing part comprises a sealing element corresponding to the outlet for sealing the outlet. More in particular, said sealing element may be so disposed that it seals the outlet in the position in which the dosing part and the supply part are joined together. This makes it possible to fill the assembly and subsequently seal it, so that the assembly can be used at a later point in time. Furthermore this makes it possible to fill a large number of assemblies with a desired dose by machine in advance. The assemblies can subsequently be sealed and transported before mixing the dose with a container substance in a container.

According to another embodiment, the dosing part comprises a dose container for receiving the dose. The dose container may be a suitably shaped space provided with a filling opening in the dosing part of the assembly.

According to one embodiment of the invention, the sealing element in the dosing part may furthermore be disposed outside the dose container. This achieves that the sealing element seals the outlet of the supply part in the joined condition of the dosing part and the supply part, without an amount of the dose remaining behind in the outlet of the supply part. The entire dose will thus be contained in the pressure chamber of the assembly. The sealing element may for example be formed by an end of a sealing part extending outwards from the dose container. If the pressure chamber is formed by the dose container on the one hand and a wall of the supply part comprising the outlet on the other hand, the sealing part extending outside the dose container can effectively seal the outlet without the possibility of a dose column remaining behind in the outlet above the sealing element.

According to another embodiment, the dosing part comprises a base and at least one container wall surrounding the base for forming the dose container. In this way a container is obtained which can function as a dose container, and which has a large filling opening for filling the dose container. Although this aspect will not be used in all cases, it has the advantage that the dose container can be easily cleaned and possibly be recycled after use.

According to another embodiment, the supply part comprises at least one side wall, which at least one side wall is so configured that the dose container is surrounded by the side wall so as to form the pressure chamber in the position in which the supply part and the dosing part are joined together. To prevent mixing substance from adhering to the wall, it is advantageous if the supply part is similarly configured, since the supply part can be placed over the dosing part in such a manner that the mixing substance will not come into contact with the wall of the supply part when the dosing part and the supply part are joined together. When the supply part is placed over the dosing part, the dose will remain in the dose container in its entirety and cannot adhere to the wall of the supply part, so that the entire dose will be present in the pressure chamber of the assembly after the supply part and the dosing part have been joined together.

The side wall may in particular be formed to mate with the dose container, so that the dose container can be received in the side wall without play. Such a connection free from play makes it possible to achieve an adequate seal of the pressure chamber of the assembly. Furthermore, a pressure difference can thus be created between the pressure inside the chamber and the pressure outside the chamber, for example the outside air, in that air is prevented from being sucked in due to the fact that the dose container is received in the supply part without play. This improves the pumping action obtained by means of the assembly according to the invention. In particular, said at least one side wall may be configured to mate with the container wall of the dose container so as to receive said container wall therein without play.

According to another embodiment of the invention, the dosing part comprises an outer wall for receiving at least part of the supply part therein in the position in which the dosing part and the supply part are joined together. In particular, the outer wall may for example be arranged for receiving the side wall of the supply part therein. In combination with the above-described embodiment in which the side wall of the supply part in closes the container wall of the dose container, a compact and solid unit is obtained in this manner, from which the mixing substance cannot escape. If according to another embodiment the outer wall of the dosing part is configured to mate with the supply part in such a manner that it is received therein without play, an adequate airtight seal from the outside air can be obtained again.

According to another embodiment, the assembly comprises locking means for locking the dosing part and the supply part in position relative to each other when the dosing part and the supply part are joined together. The advantage of this is that when the supply part and the dosing part are joined together, and the sealing element of the dosing part effectively seals the outlet of the supply part, the assembly can be locked in position, so that the sealing element cannot become detached from the outlet during transport of the assembly. As a result, leakage from the assembly is not possible in the locked position thereof.

Such locking means may for example consist of a receiving part, for example a lip, which mates with a receiving element, for example an element which encloses the lip, which receiving part is present on the dosing part of the assembly and which receiving element is present on the supply part, for example, or vice versa.

According to another embodiment, the assembly further comprises guide means for guiding a movement of the dosing part with respect to the supply part. The guide means may be formed by a guide rail and a guide cam having a shape corresponding to that of the guide rail, for example, which guide rail is placed on either one of the supply part and the dosing part, and which guide cam is placed on the other one of said supply part and said dosing part.

The advantage of using guide means is that the movement to be carried out between a supply part and a dosing part is limited by the guide means, as a result of which said movement can take place in a more efficient manner.

In particular, the guide means may be provided with stop means for preventing the supply part and the dosing part from being disconnected from each other during movement of the dosing part with respect to the supply part. As a result, the supply part and the dosing part are prevented from becoming detached from each other, so that unnecessary waste of the contents thereof is prevented.

In another embodiment of the invention, the assembly further comprises a connecting part which comprises an inlet for receiving at least the outlet of the supply part therein and connecting means for connecting the connecting part to the container. The inlet is in this embodiment arranged for providing a supply opening in the container when the connecting part is connected to the container.

In this way the assembly can be easily detached from the container after the dose has been mixed with the container substance. In particular, the container substance can be sucked into the dose container after mixing, and the supply part that is connected to the dosing part can be detached from the connecting part. The mixture will be present in the assembly of container part and dosing part in that case, whilst the connecting part will remain connected to the container (and may or may not seal it). Since the supply part and the dosing part also form a "pump" together, the assembly, with the connecting part disconnected therefrom, can be used as a squirt, whose contents can be easily transferred to another container or, for example, to a surface.

According to a second aspect of the invention, the invention provides a method for introducing a mixing substance into a container by means of an assembly according to any one of the preceding claims, said assembly comprising a dosing part and a supply part, which supply part comprises an outlet for introducing the dose into the container, characterised in that the method comprises the steps of: introducing the dose into the dosing part of the assembly; joining the dosing part and the supply part together, in such a manner that a pressure chamber whose volume can be changed is formed adjacent to the outlet by the joined supply part and dosing part for containing the dose therein; introducing one end of the outlet into a container; and moving the dosing part with respect to the supply part for the purpose of changing the volume of the pressure chamber so as to obtain a pumping action for transferring the dose to the container.

After the container substance has been transferred to the chamber, it may be returned to the container again in the above-described manner. This procedure may be repeated a few times, if required.

Using the method according to a second aspect of the invention as described above, an adequate mixing of the mixing substance with the contents of the container can obtained.

BRIEF DESCRIPTION OF THE DRAWINGS

The invention will now be described in more detail on the basis of non-limitative embodiments thereof, with reference to the appended drawings, in which.

DETAILED DESCRIPTION OF THE DRAWINGS

Figure 1:
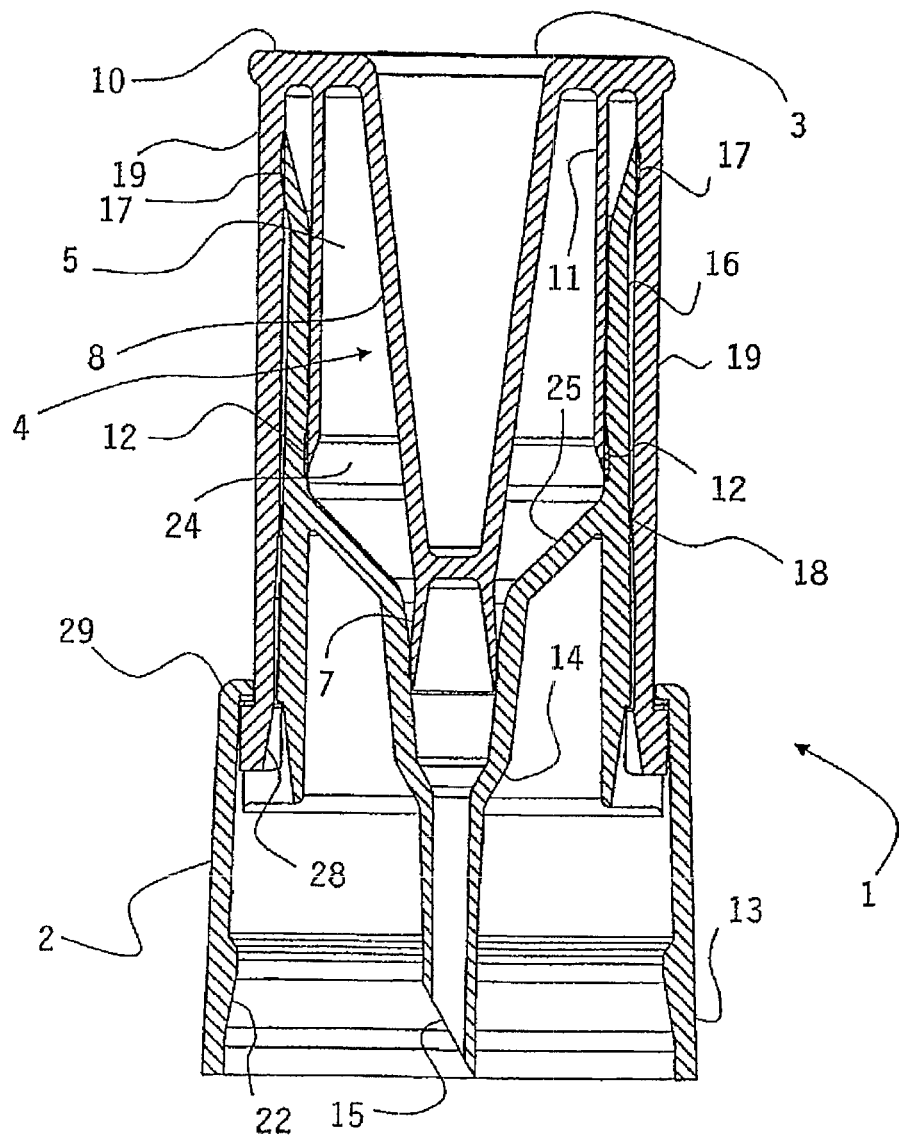
FIG. 1 is a schematic, sectional view of an assembly according to the invention.

The appended FIG. 1 shows an assembly 1 for introducing a dose of a mixing substance (schematically indicated by the arrow 4) into a container (not shown). The assembly consists of a supply part 2 and a shaped dosing part 3 that mates therewith.

The dosing part 3 comprises a dose container 5 made up of a base 10 with a circular container wall 11 extending transversely thereto. Together they define the volume that forms the dose container 5. When the dosing part 3 is detached from the supply part 2, the dose container 5 is readily accessible for being filled with a precisely metered dose of a mixing substance 4.

Furthermore, a sealing part 8 extends from the base 10 of the dosing part 3, through the dose container 5 to outside the dose container 5. Present at the end of the sealing part 8 is a sealing element 7. The sealing part 8 and the sealing element 7 are circularly symmetrical in the illustrated embodiment, just like the container wall 11. The volume of the dose container 5 thus consists of the volume defined by the base plate 10 and the container wall 11 minus the volume of the portion of the sealing part 8 that is positioned within the dose container 5. The sides of the sealing part 8 and the container wall 11 of the dosing part that face towards the dose container 5 are smooth, such that hardly any mixing substance will remain behind thereon when the dose container 5 is being emptied.

The supply part 2 consists of a housing 13, which may be so configured, for example at the end thereof, that a socket 22 is formed for receiving a container (not shown) therein. The supply part 2 furthermore comprises an outlet 14, which extends in the direction of the container, in line with the sealing element 7 (in the joined condition of the supply part 2 and the dosing part 3). The shape of the outlet 14 of the supply part 2 has been designed to correspond to that of the sealing element 7 of the dosing part 3, such that the outlet 14 can be sealed in an effective manner with the sealing element 7 by joining the dosing part 3 and the supply part 2 together (as shown in FIG. 1). The wall of the outlet 14 is circularly symmetrically in the present embodiment as well, so that a pressure chamber 24 for containing the dose, whose volume can be changed, is formed by joining the dosing part 3 and the supply part 2 together. It is noted in this context that the outlet 14 blends with the chamber wall 25.

The end 15 of the outlet 14 provides an outlet mouth that extends into the socket 22 of the supply part 2, such that the outlet mouth 15 extends into the container in the position in which a container is placed in the socket 22 of the supply part with the upper side thereof, for example for perforating a cap, a cork or other closure of the container.

At an other end of the housing 13, the housing 13 blends with a side wall 16 of the supply part, which is shaped in such a manner that it can enclose the container wall 11 of the dosing part 3 at least partially in the joined condition of the dosing part 3 and the supply part 2, as is indicated in FIG. 1. The container wall 11 of the dosing part 3 may comprise a clamping edge 12 at the end thereof, which clamping edge clamps down on the side wall 16 of the supply part 2 when the dosing part 3 is placed on the supply part 2. In this way it is possible to obtain an adequate seal, possibly even airtight seal, if desired. Likewise, the dosing part 3 comprises an outer wall 19, which extends in the direction of the supply part (in the joined condition of the dosing part 3 and the supply part 2) and which encloses the side wall 16 of the supply part. The side wall 16 of the supply part 2 similarly comprises a clamping edge 17, which clamps down on the outer wall 19 of the dosing part 3 when the supply part 2 and the dosing part 3 are joined together. In the joined condition of the dosing part 3 and the supply part 2, in which said parts 2 and 3 are in full contact with each other, a solid seal of the pressure chamber 24 in which the mixing substance is present is obtained, which mixing substance is sealed airtight from the outside air as a result of the presence of the clamping edge 12 (which clamps down on the side wall 16). The clamping edges 12 and 17 ensure that the container wall 11 and the side wall 16 are received in the side wall 16 and in the outer wall 19, respectively, without play. The clamping edge 12 functions to provide an airtight seal of the internal part of the assembly consisting of the dosing part 3 and the supply part 2. Furthermore, the outlet 14 of the supply port 2 is effectively sealed by the sealing element 7, which extends into said outlet and whose shape corresponds to that of the inner side of the outlet 14.

The clamping edge 17 moreover makes it possible to guide and position the dosing part 3 in an adequate manner with respect to the supply part 2. When the dosing part 3 is moved out sufficiently far with respect to the supply part 2, the clamping edge 17 will abut against the thickening 18 on the outer wall 19, so that the dosing part 3 is to a certain extent prevented from being moved out any further. In this way a "stop" is provided upon movement of the dosing part 3 and the supply part 2 with respect to each other.

It is furthermore noted that the container wall 11, the chamber wall 25 and the inner wall of the outlet 14 are so configured that only rounded corners are formed. The inner sides of the aforesaid walls are so smooth that when the mixing substance moves from the pressure chamber 24 to the container (not shown) via the outlet 14, the mixing substance will easily slide off the wall and reach the container via the outlet. This reduces the risk of residue of the dose remaining behind.

The operation of the assembly that is shown in FIG. 1 is as follows. Prior to the introduction of a precisely measured dose of a mixing substance into a container, the dosing part 3 is separated from the supply part 2, in such a manner that the dose container of 5 will be readily accessible. The dose container 5 can now be filled with a precisely measured dose. The dose container may be provided with grade marks, but a more precise verification of the amount of mixing substance that is present in the dose container can be obtained by weighing the empty dosing part, using high-precision scales, and weighing the dosing part 3 again after the dose container 5 has been filled. Based on the weight by volume of the mixing substance, for example, it is thus possible to verify precisely whether the introduced dose of mixing substance is the required dose and, more particularly, to determine the exact weight and volume thereof. If it is established after said filling and verification that the dose 4 that has been introduced into the dose container 5 is not correct, the dose can be easily adapted.

After the dose 4 has been introduced into the dose container 5, the supply part 2 is slid over the dosing part 3, such that the side wall 16 (as indicated in FIG. 1) is received in the space between the container 11 and the outer wall 19 of the dosing part. To obtain a proper seal of the outlet 14 of the dose part, the supply part 2 is moved sufficiently far into the dosing part 3, such that it can be locked in position by the locking means. Locking the dosing part 3 and the supply part 2 in position relative to each other prevents leakage of mixing substance of the dose 4 via the outlet during transport of the assembly. After all, the outlet 14 is sealed by the sealing element 7, which cannot come loose during transport as a result of the locking engagement. Consequently, the entire dose 4 of the mixing substance is contained in the pressure chamber 24 formed by the assembly, which pressure chamber is defined by the dose container 5 of the dosing part and the chamber wall 25 of the supply part, which terminates in the sealed outlet 14.

More in particular, the base wall 10 of the dosing part 3 is so configured that it imparts stability to the assembly when the base 10 of the assembly is placed on a supporting surface. Furthermore it provides additional advantages, for example during transport of the assembly.

To introduce the dose 4 into a container (not shown), the opening of the container (for example the end of a bottleneck) is received in the socket 22 of the supply part 2, in such a manner that the outlet mouth 15 of the outlet 14 is positioned in front of the opening or extends into said opening. In those cases in which the container is closed by a cork, a cap or other closure, the outlet 14 may be so designed that it can perforate said cork of said cap or that it opens into an opening in the cap whose shape corresponds to that of the outlet mouth 15 of the supply part. The socket 22 may be provided with connecting means (28, 29) to ensure that a solid connection which cannot easily come loose is obtained between the assembly and the container. This makes it easier to carry out the method for introducing the dose 4.

Once the container has been secured in place as a result of the opening of the container being received in the socket 22 of the supply part 2, the sealing element of 7 can be detached from the wall of the outlet by a short pull on the dosing part 3 in a direction away from the supply part 2, thereby placing the pressure chamber 24 containing the dose 4 of the mixing substance and the outlet 14 in open communication with each other. The dose 4 can now be transferred to the container (not shown) by moving the dosing part 3 to and fro with respect to the supply part 2 for increasing and decreasing the volume of the pressure chamber. In this way a pumping action is obtained, which drives the dose 4 through the outlet 14.

As already described before, the clamping edge 17 ensures that the dosing part 3 is correctly guided and positioned with respect to the supply part 2. When the dosing part 3 is moved out sufficiently far with respect to the supply part 2, the clamping edge 17 will abut against the thickening 18 on the outer wall 19, so that the dosing part 3 is to a certain extent prevented from being moved out any further. In this way a "stop" is provided, which prevents the user from accidentally pulling out the dosing part 3 too far and disconnecting the dosing part from the supply part upon doing so. Consequently, the provision of the thickening 18 on the outer wall 19 has a positive effect on the use of the assembly 1. If the user wishes to disconnect the dosing part 3 from the supply pipe 2, he can do so by pulling the clamping edge 17 over the thickening 18 by exerting a certain amount of force.

If the supply part 2 and the dosing part 3 are locked in position relative to each other, the locking engagement must be released before the dosing part 3 can be moved with respect to the supply part 2. The manner in which this can be done depends on the locking means that are used and will be known to those skilled in the art. To give an example of said locking and releasing, the supply part 2 may comprise receiving means (29), for example, which are present on the outer side of the housing 13, for example, with the outer wall 19 of the dosing part 3 similarly comprising a receiving part (28) (a lip)

that can be received in the receiving means (29). In this way a bayonet fitting is obtained. The locking engagement can be released by rotating the supply part 2 with respect to the dosing part 3, for example in a preferred direction, making it possible to move the dosing part 3 with respect to the supply part 2, such that the sealing element 7 will become detached from the inner wall of the outlet 14 and the desired pumping action can be obtained.

The pumping action can be obtained in that the clamping wall 12 of the container wall 11 clamps down on the side wall 16 in such a manner as to prevent air from being sucked in from the atmosphere surrounding the assembly. Assuming that the mixing substance in the pressure chamber 24 is present in front of and in the outlet 14, so that a part of the pressure chamber 24 (for example of part of the dose container a 5 near the base 10) is filled with air, the volume of the pressure chamber 24 can be increased by pulling the dosing part 3 back with respect to the supply part 2. As a result of the volume increase, an underpressure is generated in the pressure chamber 24 in relation to the pressure that prevails in the container (not shown). As a result, air will be drawn in from the container via the outlet 14, such that the pressure in the pressure chamber 24 will be in equilibrium with the pressure in the container. By subsequently moving the dosing part 3 towards the supply part 2 again, the pressure in the chamber 24 will increase, such that the mixing substance that is present in front of the outlet 14 is driven through the outlet to be forcefully squirted into the container. This movement may be repeated, if necessary, until all the mixing fluid has been transferred from the chamber 24 to the container.

After the dose 4 has been transferred to the container, residue of the mixing substance may have remained behind on the walls of the dose container 5, in the outlet 14 or on the chamber wall 25. This risk has already been minimised, however, because the walls of the assembly are so configured that there are no sharp corners where mixing fluid can accumulate, and because the walls of the dose container 5, the sealing part 8, the chamber wall 25 and the inner wall of the outlet are so smooth that the mixing substance will not easily adhere thereto. However, in order to ensure that the entire dose 4 of the mixing substance is transferred to the container, it is possible, for example, to turn the assembly 1 and the container (not shown) fitted therein upside-down in its entirety, in such a manner that the base of the dosing part points to the ground. Subsequently the contents of the container can be transferred to the pressure chamber again by pumping, i.e. by moving the dosing part 3 with respect to the supply part 2 in such a manner that the volume of the pressure chamber 24 increases. By pumping the contents of the container (being the mixture of the dose 4 and a container substance) from the container into pressure chamber 24 and vice versa one or more times in this manner, the pressure chamber 24 and the outlet 14 can be rinsed out.

Using the method as described above, it can be ensured that a dose 4 that has been introduced into the dose container 5 of the dosing part 3 can be transferred to a container in its entirety. Furthermore, the design of the assembly, in particular of the dosing part 3 thereof, makes it possible to introduce a dose of a mixing substance into the assembly in a very precise manner. The assembly according to the invention thus makes it possible to mix a dose of a mixing substance with the contents of the container with a high degree of precision.

Figure 2:
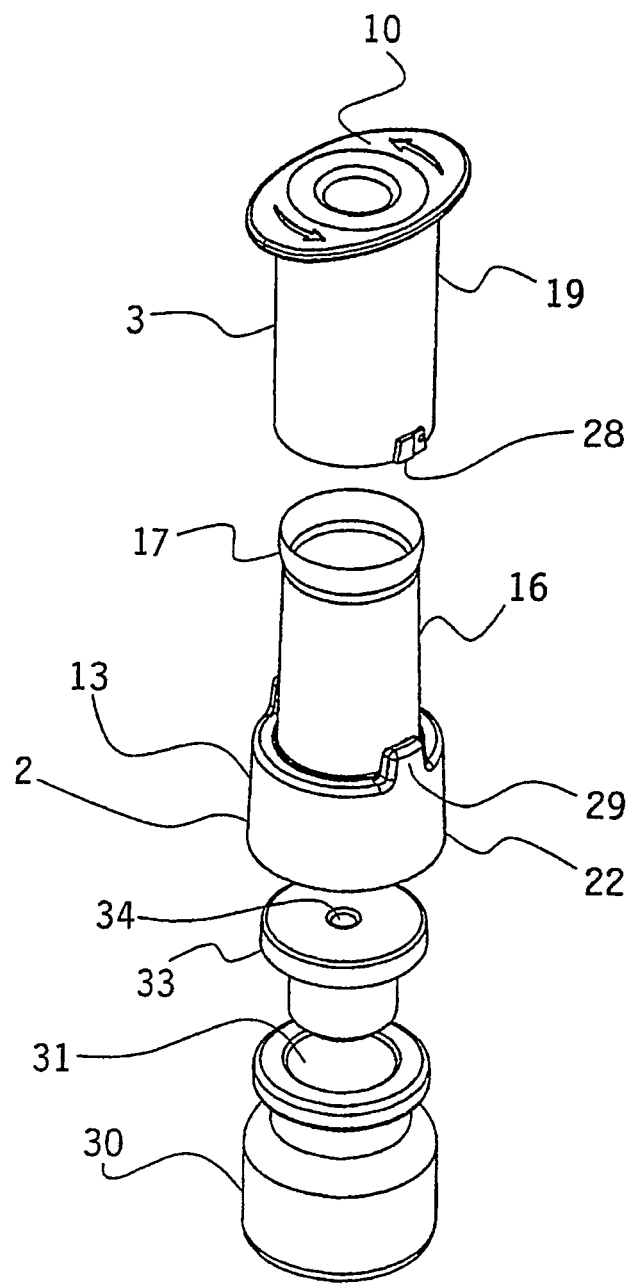
FIG. 2 is an exploded, schematic view of an assembly according to the invention and a container.

FIG. 2 is an exploded view of an assembly according to the invention, including a sealable container. In FIG. 2, those parts that correspond to parts shown in FIG. 1 are indicated by the same numerals.

FIG. 2 again shows a dosing part 3, only the base 10 and the outer wall 19 of which are shown in FIG. 2. Of the supply pipe 2, only the housing 13 comprising the socket 22 is shown in FIG. 2, as well as the side wall 16 provided with the clamping edge 17.

In FIG. 2, a first part of a bayonet fitting 28 is shown on the outer wall 19 of the dosing part 3. The bayonet 28 fits into the receiving means 29 of the supply part 2. To lock the dosing part 3 in position relative to the supply part 2, the dosing part 3 must be slid over the supply part 2 in its entirety and subsequently be rotated clockwise with respect to the supply part 2, such that the bayonet 28 is received in the receiving means 29 in its entirety. This movement provides the locking engagement.

FIG. 2 furthermore shows a container 30 having a container opening 31 into which a cap or a cork 33 fits. The cap 33 comprises a perforation 34, into which the outlet mouth (such as the outlet mouth 15 in FIG. 1) of the outlet present in the supply part 2 (not shown in FIG. 2) can be received for introducing the mixing substance.

Figure 3:
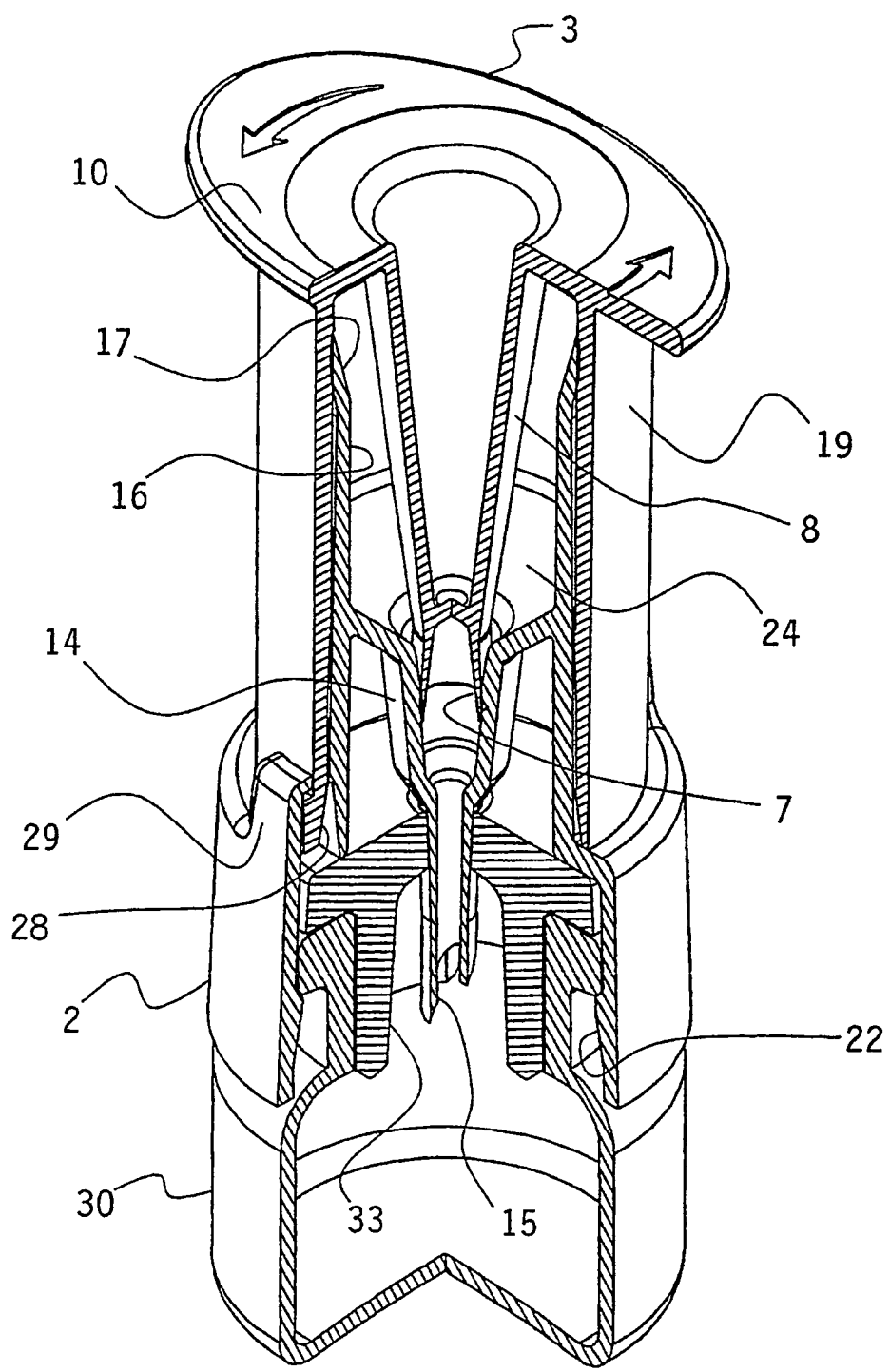
FIG. 3 is another, partially cutaway view of an embodiment according to the invention.
Figure 4:
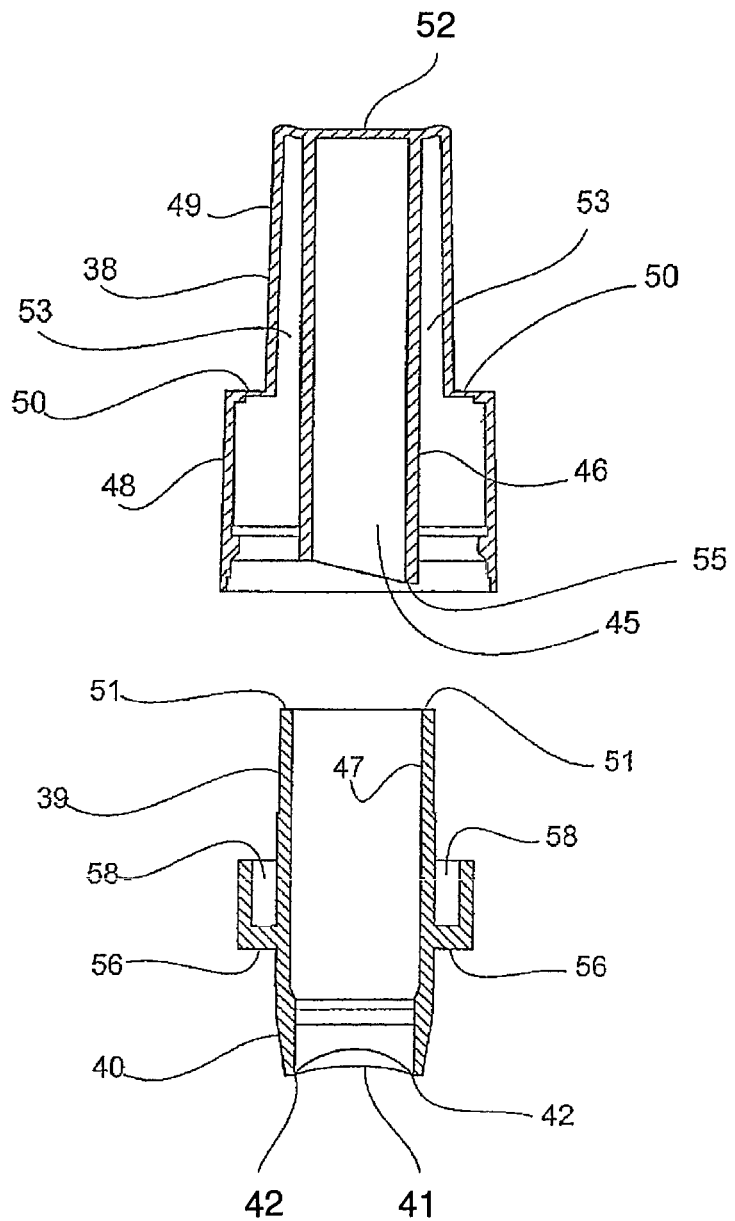
FIG. 4 shows an assembly according to the prior art.

FIG. 3 is a cutaway (quarter sectional) view of a second embodiment of the present invention. In this figure, too, those parts of the assembly that correspond to parts of the assembly that is shown in FIG. 1 are indicated by the same numerals. The embodiment that is shown in FIG. 3 only differs from the embodiment that is shown in FIG. 1 in that the container wall 11 provided with the clamping wall 12 is not present in the embodiment of FIG. 3. Tests carried out with such an embodiment have shown that incorporating the container wall 11 in the dosing part has advantages, to be true, in the sense that although this reduces the risk of mixing substance remaining behind in the assembly, which mixing substance is not mixed with the contents of the container 30, the use of such a container wall is not necessary in order to obtain an adequate operation. An advantage of the embodiment that is shown in FIG. 3 is for example the fact that it is even easier to fill the dose container 5 of the dosing part 3, since the filling opening thereof is larger.

FIG. 3 furthermore clearly shows that the outlet mouth 15 of the outlet 14 is so configured that a closure of a container can be perforated in an effective manner therewith.

The invention may be implemented in a multitude of different embodiment. In addition to the foregoing, for example, a connecting part may be provided, by means of which the supply part can simply be fitted in a container. Such a connecting part may in particular consist of a socket for receiving an opening of the container therein. The connecting part may also comprise an inlet for receiving the outlet of the supply part therein. Furthermore, the connecting part and the supply part may be so configured in that case that they can be locked in position relative to each other; for example by means of a bayonet connection or a threaded connection. When such an embodiment (not shown in the above-described figures) is used, the supply part that is connected to the dosing part can be evenly detached from the connecting part that is connected to the container. The supply part and the dosing part, when combined, can be used as a squirting instrument, as a result of the pumping action therebetween, if the dosing part has been filled with, for example, the container substance before the connecting part and the supply part are disconnected from each other. The connecting part may seal the container in that case.

Figure 5A:
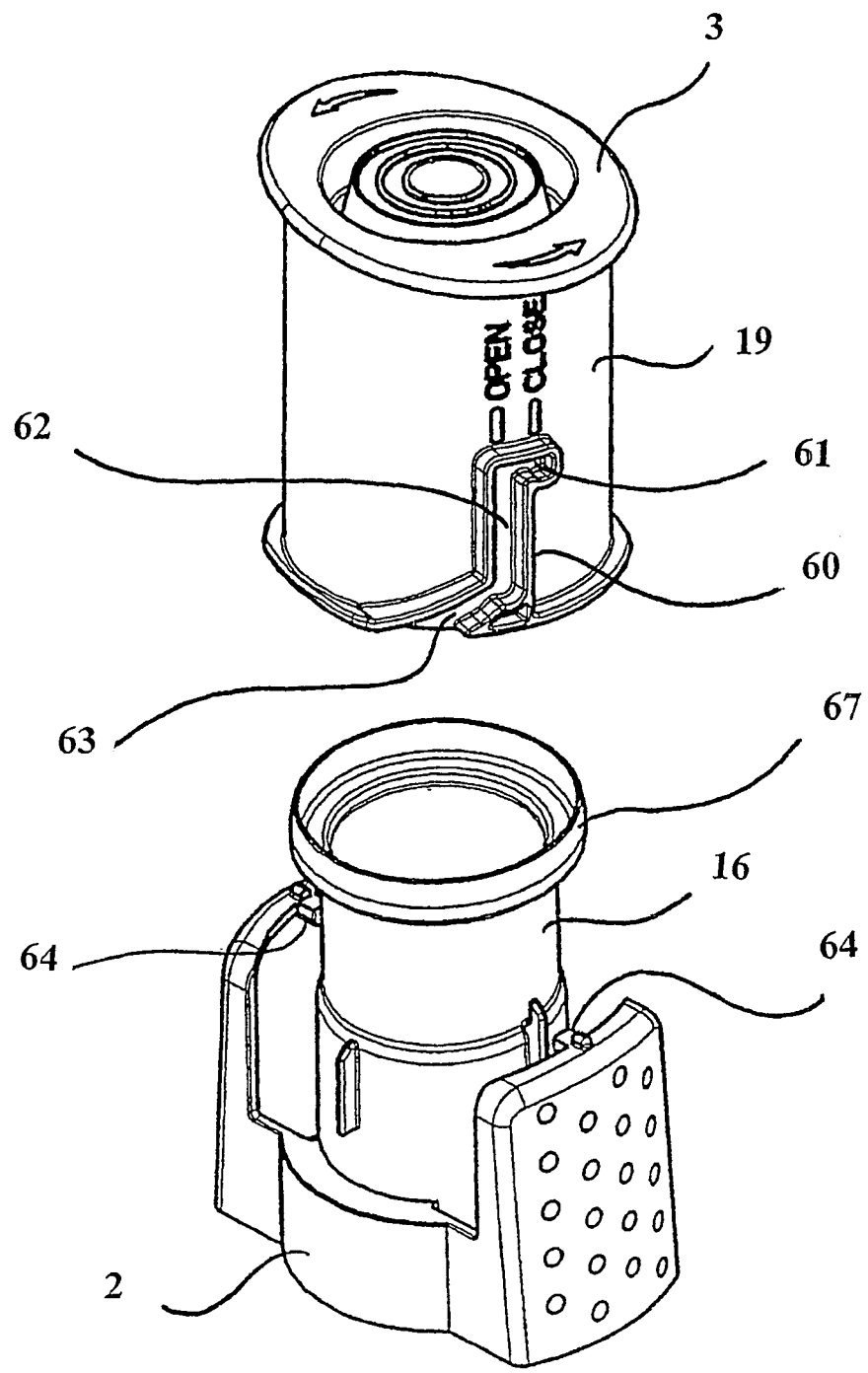
FIG. 5A shows another embodiment according to the invention.

FIG. 5A shows another embodiment of the assembly according to the invention, which embodiment is provided with guide means 60. The guide means 60 consist of two guide rails 62 formed on the outer wall 19 of the dosing part 3 (one of which is hidden from view, so that only one is shown), and two correspondingly shaped guide cams 64 on the supply part. The guide rails are configured to form a stop 63 at the end of the outer wall 19. The stop 63 of the rail 62 blends with a straight part of the rail in the extension thereof, which straight part extends parallel to a longitudinal axis through the dosing part. Located at the other end of the guide rail is a locking part 61. The locking part 61 is so configured that when the dosing part 3 is slid over the supply part 2 in its entirety, the cams 64 can be locked in position in the locking part 61 by rotating the dosing part 3 with respect to the supply part 2.

In use, the assembly can be filled with a fluid by disconnecting the dosing part 3 from the supply part 2, thereby enabling access to the dose container 5 (not shown in FIG. 5a). The assembly can be sealed by placing the dosing part 3 on top of the supply part 2, in such a manner that the cams 64 slip into the stop 63 of the guide rails 62, and rotating the dosing part slightly with respect to the supply part. The dosing part 3 can then be moved in the longitudinal direction with respect to the supply part 2, the movement being limited by the guide rail. To lock the assembly in position, the dosing part 3 is slid over the supply part 2 in its entirety, and the dosing part 3 is slightly rotated again, so that the cams 64 are locked in position in the locking part.

Figure 5B:
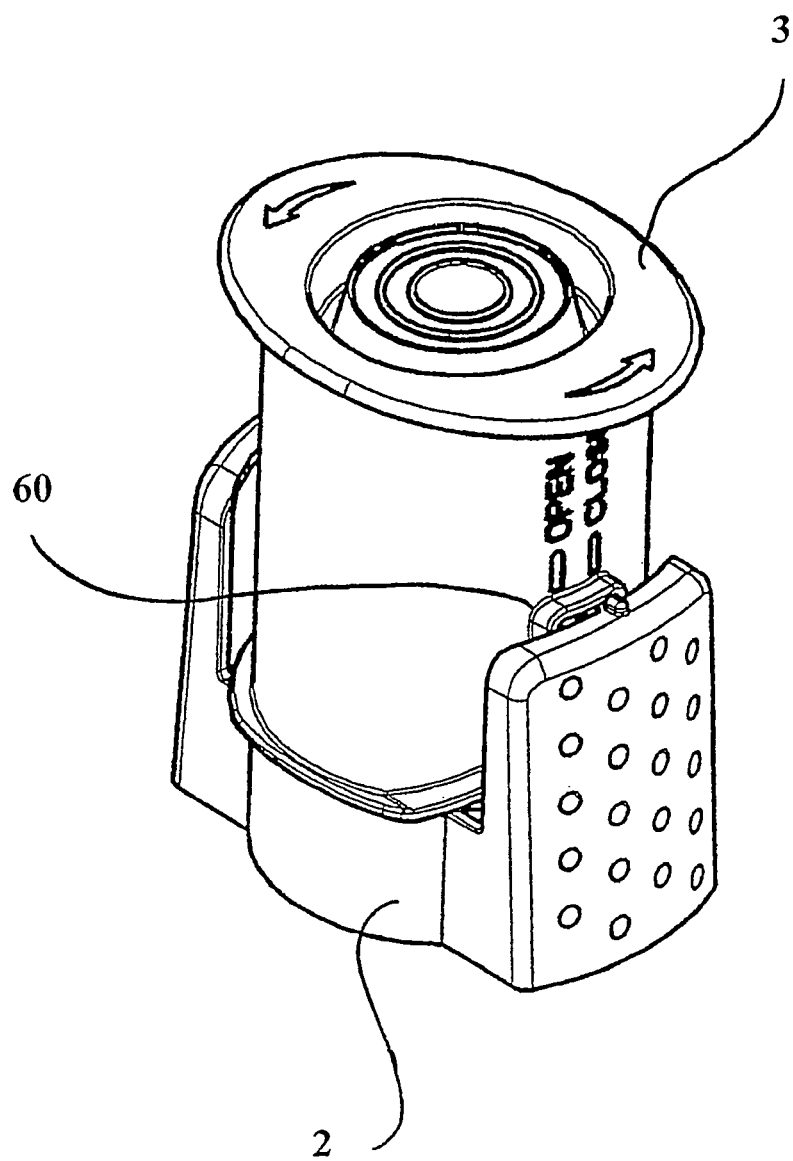
FIG. 5B shows the assembly of FIG. 5A with the parts thereof in the moved-together position.

The advantage of this embodiment is that the stop 63 ensures that the dosing part 3 cannot become detached from the supply part 2 upon providing the pumping action by moving the dosing part 3 with respect to the supply part 2. In the embodiment of FIG. 5A, the clamping edge 17 has been substituted for an alternative clamping edge 67, which has more or less the same function as the clamping edge 17. FIG. 5B shows the assembly of FIG. 5A, in which the dosing part 3 is slid over the supply part 2 in its entirety and is locked in position in the guide means 60.

The embodiments that are shown in the figures are merely intended by way of illustration of the system according to the invention as described herein. Those skilled in the art will appreciate that the design described herein can be easily modified without departing from the inventive concept. Thus it will be apparent to those skilled in the art that an assembly according to the invention may be made of various materials, for example comprising polyethylene, such as high-density polyethylene (HDPE), or polypropylene. A person skilled in the art may in particular use materials having a low water permeability, which has a positive effect on the shelf life of the dose contained in the assembly. Accordingly, the scope of the invention described herein is limited only by the appended claims. It will be understood that the embodiments as shown and described herein must not be construed as limiting the invention.

The invention claimed is:

1. An assembly for introducing a dose of a mixing substance into a container, said assembly comprising a dosing part and a supply part, which dosing part is arranged for receiving the dose and which supply part comprises a chamber wall and an outlet for introducing the dose into the container, wherein the dosing part and the supply part are configured to cooperate with one another, such that a pressure chamber having a changeable volume is formed adjacent to the outlet when the supply part and the dosing part are joined together, and wherein the dosing part is adapted to move toward and away from the supply part to decrease and increase the volume of the pressure chamber for enabling a pumping action for pumping the dose into and out of the pressure chamber;

wherein said chamber wall of said supply part blends into said outlet and the chamber wall and the outlet comprise smooth inner sides and rounded corners for reducing a risk of residue of said dose remaining in said supply part, wherein the dosing part comprises a sealing element corresponding to the outlet and in detachable engagement with an inner wall of the outlet, the sealing element is configured to seal the outlet, and the detachable engagement of the sealing element and the inner wall of the outlet enables said pumping action for pumping the dose into and out of the pressure chamber, and wherein the sealing element in the dosing part is disposed outside a dose container portion of the dosing part.

2. An assembly according to claim 1, wherein the dosing part comprises a dose container for receiving the dose.

3. An assembly according to claim 1, wherein the sealing element is formed by an end of a sealing part extending outwards from the dose container portion of the dosing part.

4. An assembly according to claim 2, wherein the dosing part comprises a base and at least one container wall surrounding the base for forming the dose container.

5. An assembly according to claim 1, wherein the supply part comprises at least one side wall and wherein the dosing part is at least partially receivable in the side wall of the supply part without play so as to form the pressure chamber.

6. An assembly according to claim 2, wherein the sealing element is formed by an end of a sealing part extending outwards from the dose container portion of the dosing part and wherein the dose container portion of the dosing part is at least partially receivable in the side wall of the supply part without play so as to form the pressure chamber.

7. An assembly according to claim 5, wherein the dosing part furthermore comprises an outer wall for receiving at least part of the side wall of the supply part therein.

8. An assembly according to claim 7, wherein the side wall of the supply part is receivable in the outer wall of the dosing part without play.

9. An assembly according to claim 1, further comprising a locking device configured to lock the dosing part and the supply part in position relative to each other when the dosing part and the supply part are joined together.

10. An assembly according to claim 9, wherein the locking device comprise a receiving part that mates with a receiving element.

11. An assembly according to claim 9, wherein the locking device are arranged for locking the dosing part and the supply part in position relative to each other, in such a manner that the sealing element seals the outlet in the locked position of the assembly.

12. An assembly according to claim 1, further comprising a guide device configured for guide a movement of the dosing part with respect to the supply part.

13. An assembly according to claim 12, wherein the guide device are formed by a guide rail and a guide cam having a shape corresponding to that of the guide rail, which guide rail is located on either one of the supply part and the dosing part, and which guide cam is located on the other one of said supply part and said dosing part.

14. An assembly according to claim 12, wherein the guide device are provided with a stopper configured to prevent for the supply part and the dosing part from being disconnected from each other during movement of the dosing part with respect to the supply part.

15. An assembly according to claim 1, wherein the dosing part is made in one piece.

16. An assembly according to claim 1, wherein the supply part is made in one piece.

17. An assembly according to claim 1, wherein at least either one of the dosing part and the supply part is made of the material comprising polyethylene, such as high-density polyethylene (HDPE), or polypropylene.

18. An assembly according to claim 1, further comprising a connecting part which comprises an inlet for receiving at least the outlet of the supply part therein and connecting means for connecting the connecting part to the container, wherein the inlet is arranged for providing a supply opening in the container when the connecting part is connected to the container.

19. The assembly according to claim 1, wherein the container is not part of the assembly, but is a separate structure and wherein the assembly is adapted to be connected to the separate container structure.

20. A method for introducing a mixing substance into a container by means of an assembly according to any one of the preceding claims, said assembly comprising a dosing part and a supply part, which supply part comprises an outlet for introducing the dose into the container, the method comprising the steps of:
    introducing the dose into the dosing part of the assembly;
    joining the dosing part and the supply part together, in such a manner that a pressure chamber having a changeable volume is formed adjacent to the outlet by the joined supply part and dosing part for containing the dose therein;
    introducing one end of the outlet into a container; and
    moving the dosing part toward and away from the supply part for changing the volume of the pressure chamber so as to obtain a pumping action for transferring the dose to the container and, after the dose has been transferred to the container, the mixture of the dose and the container substance that is present in the container can be pumped back into the pressure chamber,
    wherein the dosing part comprises a sealing element corresponding to the outlet and in detachable engagement with an inner wall of the outlet, the sealing element is configured to seal the outlet, and the detachable engagement of the sealing element and the inner wall of the outlet enables said pumping action for pumping the dose into and out of the pressure chamber, and
    wherein the sealing element in the dosing part is disposed outside a dose container portion of the dosing part.

21. A method according to claim 20, wherein the container contains a container substance that is to be mixed with the dose so as to obtain a mixture consisting of the container substance and the dose, and wherein the method further comprises the step of moving the dosing part with respect to the supply part after the dose has been transferred to the container for the purpose of changing the volume of the pressure chamber, so that the mixture is pumped back into the pressure chamber for rinsing out the pressure chamber.

22. A method according to claim 21, further comprising the step of moving the dosing part with respect to the supply part after the mixture has been transferred to the pressure chamber for the purpose of changing the volume of the pressure chamber, so that the mixture is pumped back into the container again.

23. A method according to claim 22, wherein at least one of the steps of claim 21 is repeated one or more times so as to obtain a desired concentration ratio between the dose and the container substance in the mixture.

* * * * *